United States Patent [19]

Yamamoto et al.

[11] Patent Number: 4,536,474
[45] Date of Patent: Aug. 20, 1985

[54] TISSUE CULTURE OF LICHENS

[75] Inventors: Yoshikazu Yamamoto; Ryuzo Mizuguchi, both of Neyagawa; Yasuyuki Yamada, Uji, all of Japan

[73] Assignee: Nippon Paint Co., Ltd., Osaka, Japan

[21] Appl. No.: 431,096

[22] Filed: Sep. 30, 1982

[30] Foreign Application Priority Data

Sep. 30, 1981 [JP] Japan ............... 56-156765
Oct. 27, 1981 [JP] Japan ............... 56-172605
Oct. 27, 1981 [JP] Japan ............... 56-172606

[51] Int. Cl.$^3$ ............... C12P 39/00; C12P 19/04; C12P 17/18; C12P 17/02; C12P 7/62; C12P 7/40; C12P 7/44; C12P 7/42; C12P 7/26; C12P 7/22; C12P 17/08; C12P 17/06; C12P 17/04; C12P 7/64; C12N 5/00; C12R 1/645; C12R 1/89; A01G 7/00; A01H 13/00; A01B 79/00; A01C 1/00

[52] U.S. Cl. ............... 435/42; 435/101; 435/119; 435/123; 435/124; 435/125; 435/126; 435/134; 435/135; 435/136; 435/142; 435/146; 435/148; 435/156; 435/240; 435/911; 435/946; 47/1.4; 47/58

[58] Field of Search ............... 47/1.4, 58; 435/174–182, 946, 911, 240, 243, 101, 119, 123, 124, 125, 126, 134, 135, 136, 142, 146, 148, 156

[56] References Cited

U.S. PATENT DOCUMENTS 4,148,689  4/1979  Hino et al. ............... 435/182

OTHER PUBLICATIONS

Ahmadjian, V., *The Lichen Symbiosis*, pp. 92–93, 1967.
Ahmadjian, V., "Artificial Reestablishment of Lichen Cladonia Cristatella", Science, 151, pp. 199–201, (1966).
Brodelius, P., et al., "Entrapment of Plant Cells in Different Matrices," Febs Letters, 122(2), pp. 312–316, (1980).
Asahina, Y. et al., Chemistry of Lichen Substances, pp. 3–9, (1954).
Singleton, P. et al., Dictionary of Microbiology, pp. 223–225, (1978).

*Primary Examiner*—Thomas G. Wiseman
*Assistant Examiner*—Jayme A. Huleatt
*Attorney, Agent, or Firm*—Wenderoth, Lind & Ponack

[57] ABSTRACT

An undifferentiated symbiotic combination of alga and fungus cells, obtained directly from a lichen explant, are cultured in a media under appropriate conditions to produce aromatic lichenous substances and these substances are recovered.

9 Claims, 1 Drawing Figure

FIG. 1

TISSUE CULTURE OF LICHENS

The present invention relates to an undifferentiated symbiont induced from the tissue of lichen flora, and its production.

Lichens are the plants which are characterized by the symbiont consisting of fungi and algae, and hence occupy an unusual position in botany. According to the microscopic observation, lichens differentiate varieties of tissues including cortex (a tissue covering and protecting the thallus and consisting of gathered and adhered hyphae), algal layer (a tissue in which algae in the thallus are surrounded and supported by hyphae), medulla (a basic tissue of thallus consisting of loosely entangled hyphae) and rhizine (a tissue projecting on the under-side surface and sticking the thallus on a carrier), which are the structural characteristics of lichens. (But, in some cases, the under-side surface of thallus do not have rhizina.)

Lichenous substances, which are the metabolic products of lichens, are different from the most of higher or lower plant substances and belong to a special, limited chemical division. According to Asahina (Asahina and Shibata, "Chemistry of Lichenous Subsrances", Kawade Shobo, 1948), the lichenous substances may be classified into the following groups:

A. Aliphatic lichenous substances:
 Group 1. Acids
  (a) Monobasic lactone-acids
  (b) Dibasic acids
  (c) Tribasic acids
 Group 2. Neutral compounds which show Liebermann's reaction (Zeorin compounds)
 Group 3. Polyhydric alcohols
B. Aromatic lichenous substances:
 Group 1. Pulvic acid derivatives
 Group 2. Depsides
  (a) Orcin compounds
  (b) Orcin-β-orcin mixed compounds
  (c) β-Oricin compounds
 Group 3. Depsidones
  (a) Orcin compounds
  (b) β-Orcin compounds
 Group 4. Quinones
  (a) Oxyanthraquinones
  (b) Phenanthrene quinones
 Group 5. Xanthone derivatives
 Group 6. Diphenyleneoxide derivatives
 Group 7. Nitrogen containing compounds (Diketopiperadine derivatives)
C. Carbohydrates:
 Group 1. Polysaccharides

More precisely, the following compounds are included as the representatives in the lichenous substances:

I. DEPSIDONES:

| Compound | Structure |
|---|---|
| Variolaric acid |  |
| Norstictic acid |  |
| Pannarin |  |
| Physodalic acid |  |
| Physodic acid |  |
| Psoromic acid |  |
| Fumaroprotocetraric acid |  |
| Lobaric acid |  |
| α-Collatolic acid |  |
| Salazinic acid |  |

I. DEPSIDONES:

| Compound | Structure |
|---|---|
| Stictic acid | |
| Alectronic acid | |
| Protocetraric acid | |

II. DEPSIDES

| Compound | Structure |
|---|---|
| Hypotamnolic acid | |
| Thamnolic acid | |
| Boninic acid | |
| Homosekikanic acid | |
| Barbatic acid | |

II. DEPSIDES

| Compound | Structure |
|---|---|
| Balbatolic acid | |
| Microphyllic acid | |
| Sphaerophorin | |
| Sekikaic acid | |
| Diffractaic acid | |
| Atranorin | |
| Lecanoric acid | |
| Aniziaic acid | |
| Evernic acid | |
| Obtusatic acid | |

-continued

II. DEPSIDES

| Compound | Structure |
|---|---|
| Olivetoric acid |  |
| Baeomycesic acid |  |
| Perlatolic acid |  |
| Tenniorin |  |
| Umbilicaric acid |  |

III. DIPHENYLENEOXIDES

| Compound | Structure |
|---|---|
| Strepcilin |  |
| Didymic acid |  |

-continued

III. DIPHENYLENEOXIDES

| Compound | Structure |
|---|---|
| Usnic acid |  |

IV. VULPINIC ACIDS

| Compound | Structure |
|---|---|
| Calycine |  |
| Pynastolinic acid |  |
| Rhyzocarpinic acid |  |
| Vulpinic acid (Pulvic acid methyl ester) |  |

V. ANTHRAQUINONES

[Structure: anthraquinone core]

| Compound | Structure |
|---|---|
| Rodocradonic acid | [Structure with HOH₂C, HO, OH, COOCH₃ substituents on anthraquinone] |
| Endcrotin | [Structure with HO, OH, COOH, CH₃ substituents on anthraquinone] |
| Pariethine | [Structure with HO, OH, CH₃O, CH₃ substituents on anthraquinone] |

VI. PHENANTHRENEQUINONES

[Structure: phenanthrenequinone core]

| Compound | Structure |
|---|---|
| Telephoric acid | [Structure with HO, OH, COOH, —CH=CH—CH=CH—COOH substituents] |

VII. FATTY ACIDS

| Compound | Structure |
|---|---|
| Rangiformic acid | $\left.\begin{array}{l}CH_2COOH \\ | \\ CHCOOH \\ | \\ CHCOOH \\ | \\ (CH_2)_{13}-CH_3\end{array}\right\} CH_2$ |
| Caperatic acid | $\left.\begin{array}{l}CH_2COOH \\ | \\ C(OH)COOH \\ | \\ CHCOOH \\ | \\ (CH_2)_{13}-CH_3\end{array}\right\} -CH_2-$ |

VIII. TRITERPENES

| Compound | Structure |
|---|---|
| Zeorin | [Triterpene structure with HO, OH, OH groups] |
| Ursolic acid | [Triterpene structure with HO and COOH groups] |

IX. TETRONIC ACIDS

| Compound | Structure |
|---|---|
| Protolichesterinic acid | $CH_3(CH_2)_{11}CH_2-CH$ [lactone ring with C=O, CH=CH₂, HOOC substituents] |

X. XANTHONES

[Structure: xanthone core]

| Compound | Structure |
|---|---|
| Thiophanic acid | [Structure with CH₃, CH₃O, OH, Cl substituents on xanthone] |

As for the physiological significance of the lichenous substances, it is considered that the lichenous substances may be helpful in protecting lichens from the attack of microorganisms or the consumption by small animals because growing of lichens is very slow, or that the lichenous substances are useful for protecting lichens from ultraviolet rays because lichens grow in sunny places in contrast to other fungi. Therefore, the lichenous substances have been employed in various uses such as dyestuffs, antibiotics, perfumes, etc. on the basis of the above functions.

Since the growth of lichens is very slow and is affected by natural environment such as season, climate, temperature or latitude, and artificial conditions such as sulfurous acid gas or smoke, natural cultivation of lichens is very difficult and has never succeeded. Collection of wild lichens is also difficult because much skill is required for identification of lichens due to the fact that there are numerous lichens which closely resemble each other in appearance but differ in components.

It was proposed (Yoshimura, "Lichen Flora of Japan in Color", p. 319, Hoikusha) that lichenous fungi be separated from lichenous algae and be cultured for producing the lichenous substances. However, in this method, the lichenous substances are not produced in some cases due to lack of effects obtainable by symbiosis.

Recently, the tissue culture of higher plants has been studied as a technique for producing plant substances. Since a plant tissue under culture grows much more rapidly than a natural plant, the growth of which takes months or years, the tissue culture enables the production of plant substances in a shorter period and permits prearranged production on an industrial scale without being affected by climate or needing man's power for harvesting, in contrast to natural growth. However, success in tissue culture of lichens has never been reported, although its study has been continued.

According to the invention, it has now been discovered that the tissue culture of lichens can be carried out successfully by inducing an undifferentiated symbiont from the lichenous tissue and culturing said undifferentiated symbiont in an appropriate medium, and that the symbiotic effects are fully used to activate the growth of the symbiont so that the lichenous substances are produced in an excellent yield.

Ordinary culture processes have been attempted in order to increase lichens artificially as mentioned above. However, in the conventional processes, importance has been attached to fungus cells and efforts have been continuously made to increase them. In contrast to the conventional processes, the inventors have attached importance to the relationship between fungus and alga. As the result, the inventors have succeeded in inducing the coexistent state of fungus and alga as an undifferentiated symbiont and in establishing an industrial process which allows rapid and stationary production of the lichenous substances by culturing said undifferentiated symbiont. Accordingly, the main characteristic of the invention resides in culture of the undifferentiated symbiont as a novel technical concept, and this enables the rapid and stationary production of the lichenous substances on an industrial scale. The undifferentiated symbiont itself is novel to the best of knowledge of the present inventors and culture of the undifferentiated symbiont has never been attempted. Needless to say, it has not been known that the lichenous substances can be produced favorably by culturing the undifferentiated symbionts.

As can be clearly seen from the Examples described hereinbelow, the present invention is universally applicable to various lichens belonging to a great number of families including Teloschistaceae, Physciaceae, Buelliaceae, Usneaceae, Aziaceae, Parmeliaceae, Candelariaceae, Lecanoraceae, Pertusariaceae, Acaroposoraceae, Imbilicariaceae, Cladoniaceae, Baeomycetaceae, Stereocaulaceae, Lecideaceae, Gyalectaceae, Asterothyriaceae, Stictaceae, Peltigeraceae, Pannariaceae, Coccocarpiaceae, Placynthiaceae, Heppiaceae, Collemataceae, Lichinaceae, Graphidaceae, Thelotremataceae, Diploschistaceae, Verrucariaceae, Pyrenulaceae, Strigulaceae, Sphaerophoraceae, Calidiaceae, Cypheliaceae, Lecanactidaceae, Opegraphaceae, Arthopyreniaceae, Arthoniaceae, Dictyonemaataceae, Clavariaceae, Agaricaceae and so on.

In the above and following description, the term "undifferentiated symbiont" means a system consisting of at least one alga cell and at least one fungus cell, which exhibits symbiotic effects between alga and fungus, but has not differentiated the structural characteristics in lichens.

The term "symbiotic effects" means certain synergistic effects acting between alga and fungus and activating growth of alga and fungus as well as production of metabolites. It is considered that these effects are caused by transfer of physiologically active trace substances including nutrients.

The undifferentiated symbionts of lichens used in the invention are obtained by inducing them from a lichenous plant which is used as the starting material. A practical procedure for induction of the undifferentiated symbionts is illustrated, taking *Usnea rubescens* (Usneaceae, Lecanorales) by way of example, in the followings:

Thallus of *Usnea rubescens* is washed sufficiently with deionized sterile water and cut into a small piece having an appropriate size with a sterile scalpel. The piece must include both an alga and a fungus. The piece is placed on a suitable culture medium such as a solid medium, for example, Murashige and Skoog's medium, and incubated at a constant temperature, preferably between 0° C. and 40° C. and ordinarily in light.

After about 3 weeks of culture, there are formed undifferentiated symbionts, which are transplanted sterilely on a fresh culture medium having appropriate composition and incubated at a constant temperature between 0° C. and 40° C., preferably between 20° C. and 35° C., and ordinarily in light. In a preferred embodiment, the undifferentiated symbionts obtained above are suspended in a liquid culture medium and subjected to so-called liquid culture such as stationary culture, shaking culture, agitation culture or aeration culture, because the liquid culture is suitable for production in industrial scale and symbiotic effects are more remarkable than solid culture due to quick transfer of material between alga and fungus in the symbiont.

The medium for culture of undifferentiated symbiont may be any natural or synthetic, organic or inorganic culture medium such as, for example, conventional inorganic synthetic culture medium containing organic substances such as nutrients, carbon sources and other natural extract substances within the limit of avoiding adverse affection of the symbiotic effects. Typical examples of inorganic synthetic culture medium are White's culture medium, Hildebrand's medium, Linsmaier-Skoog's medium, Murashige-Skoog's medium, etc.

Said nutrients may be vitamins such as thiamine hydrochloride, pyridoxine hydrochloride and nicotic acid, amino acids such as glycine and asparagine, hexahydric alcohols such as inositol and sorbitol, etc. Examples of said carbon sources include carbohydrates (e.g. sucrose, glucose, maltose), organic acids (e.g. acetic acid) and alcohols (e.g. methanol, glycerol). Said natural extract substances can be casein hydrolyzate, coconut milk, yeast extract, malt extract, etc. They can be used solely or in combination.

The phototrophic culture of the invention may be carried out by placing the culture in light not more than 10,000 lux, ordinarily 500–10,000 lux. As the light source, sun light, fluorescent lamp, incandescent lamp, mercury lamp or the like can be used. Ordinarily, algae do not grow without application of light. The application of light may be continuous or intermittent with a period of several hours.

When the culture of symbiont is carried out in a $CO_2$-enriched atmosphere, the symbiotic effects can be increased and the growth of symbiont is activated. Thus, it is preferable to continuously supply $CO_2$-containing air in a culturing tank. A suitable concentration of carbon dioxide gas in the air is from 0.1 to 5% (by volume), preferably from 0.5 to 2%, in order to activate the growth of the undifferentiated symbiont.

The lichenous substances may be isolated from cultured undifferentiated symbiont by any convenient or conventional method. One of practical procedures for isolating lichenous substances by solvent extraction is illustrated, taking *Usnea rubescens* by way of example, in the following:

The cultured undifferentiated symbionts are collected by filtration of culture medium and dried at 60° C. for 24 hours or at 100° C. for 3 hours in order to remove water. Then, the dried symbionts are extracted with acetone by means of Soxhelet extraction, digestion or merceration. The acetone may be replaced by other polar solvent (e.g. methanol, ethanol). The acetone extract is concentrated in order to remove acetone. The concentrate is partitioned between water and ethyl acetate. The ethyl acetate may be replaced by other organic solvents (e.g. chloroform, methylene dichloride, n-hexane, ethyl ether, benzene, methyl acetate, n-pentane, cyclohexane, petroleum ether). Then, the ethyl acetate layer is separated from aqueous layer and concentrated by evaporating ethyl acetate. The concentrate is subjected to column chromatography or thin-layer chromatography to give usnic acid as a desired lichenous substance.

The usnic acid obtained above have a melting point about 203° C. and agrees with the commercially available usnic acid in thin-layer chromatography using silica gel G with various solvent system such as hexane/ethyl/formic acid=130/80/20, hexane/ethyl acetate/formic acid=50/40/7, benzene/dioxane/formic acid=90/45/4 (all ratios being given by volume). Also, it agrees with the commercial one in infrared spectrum and nuclear magnetic spectrum. The obtained usnic acid is identified by the above analytical methods.

Still, said undifferentiated symbionts may be obtained and used in any immobilized state. It was known that various living cells can be combined with, adsorbed on or trapped in carriers such as high molecular compounds. However, in the known technique, only one kind of bacterial cells or plant or animal cells was used. Thus, it has never been attempted to immobilize the complex system of different cells, especially a symbiont. The inventors have attached importance to the fact that the lichens are symbionts of algae and fungi, and have found that the undifferentiated symbionts are easily dispersed in media as compared with the naturally occurring differentiated symbionts of lichens, and as a result, have succeeded in obtaining industrially useful immobilized plant tissue by coagulating said undifferentiated symbionts.

Immobilization may be effected by any convenient method such as carrier-bonding method, trapping method or crosslinking method, and preferably such method is selected according to purpose of usage and kind of lichens to be immobilized. For instance, when symbionts are intended to immobilize a living catalyst, immobilization is preferably effected under mild conditions in which symbiotic effects between alga and fungus are maintained, because enzymatic activity in immobilized symbionts must be stabilized.

The carrier-bonding method includes the covalent bonding method in which carrier and undifferentiated symbionts are covalently bonded together, ion bonding method in which undifferentiated symbionts are bonded by ionic reaction with a carrier having an ion-exchange group, physical adsorption method, biological adsorption method, etc., among which the most preferred is the ion bonding method. The carrier is preferably insoluble as well as porous and has a suitable pore size for capturing the undifferentiated symbionts. Suitable carriers include natural high molecular carriers (such as polysaccharide including agarose, cellulose, insoluble protein such as collagen, gelatin), synthetic high molecular carriers (such as vinyl resin, acryl resin, polyester resin, polyamide resin, epoxy resin, polyether resin, urethane resin), inorganic carriers (such as alumina, glass, avalite, bone dust, acid clay), and these may be used solely or in admixture.

The trapping method includes a method in which undifferentiated symbionts of lichens are trapped in grid of natural high molecular compound such as carrageenan or synthetic high molecular compound such as polyacrylamide gel, which are prepared by polymerization, and a method in which said symbionts are trapped in microcupsules of semipermeable membrane or hollow fiber. The trapping method is advantageous for immobilizing undifferentiated symbionts of lichens because the undifferentiated symbionts are immobilized without chemical modification and hence marring of enzymatic activity on the symbiotic form is minimized. Preferably, the carrier has a net-like structure with a suitable mesh size for capturing the undifferentiated symbionts of lichens. Such carriers include natural high molecular carriers (such as alginic acid salt, carrageenan, starch, agar, cellulose, albumin) and synthetic high molecular carriers (such as polyacrylamide, photo-crosslinking synthetic resin, radiation-polymerizing synthetic resin).

The crosslinking method is a method in which the undifferentiated symbionts of lichens are immobilized by combining the undifferentiated symbionts with each other using bifunctional reagents such as glutaraldehyde or other multifunctional reagents. Said bifunctional reagents include dialdehydes such as glutaraldehyde, imidoesters such as dimethyl adipinimidate, diethyl-d, 3'-dithiolbispropionimidate, triazines such as 1,3-dichloro-5-methoxytriazine, 1,3,5-trichlorotriazine, diisocyanates such as tolylenediisocyanate.

The carrier-bonding method, trapping method and crosslinking method are solely used in general, but may be used in combination depending upon the usage or kind of lichens. For example, the symbionts may be adsorbed on to collagen and then crosslinked with glutaraldehyde.

The immobilized lichenous tissues according to the invention are useful as a catalyst for preparing or converting primary or secondary metabolites, deodorizing agents, adsorbents for heavy metal ions, bioelectrodes and carriers for perfume, fertilizer or agricultural chemicals. In addition, industrial production of specific products may be realized by culturing undifferentiated symbionts of lichens which are trapped in polymer particles and which have high capacity for producing said specific product together with another symbionts in the same culture tank.

The invention will now be further illustrated by means of the following examples. Cultures of the undifferentiated symbionts as used in those examples are deposited at the Depository in the Technical Center belonging to Nippon Paint Co. Ltd. at Neyagawa-shi, Osaka-shi, Japan. Since any reliable method for preservation of the cultures in the state of rest has not been established, the cultures are kept in a living state. Thus, the living cultures, for instance, on slant agar media comprising malt extract (Difco) (2% w/v), yeast extract (Difco) (0.2% w/v) and agar (2% w/v) may be kept at 20° C. in a dark place and successively transplanted to the same media as above with intervals of every 20 months.

EXAMPLE 1

A piece with a length of about 1 cm was cut from thallus of *Usnea rubescens* (Usneaceae, Lecanorales) collected at Kyoto-shi (ATCC (Accession Number not available at time of filing)), and was washed sufficiently with water and rinsed several times in sterile distilled water in a sterile cup-board. The obtained explant of lichen was placed aseptically on a synthetic agar culture medium. The medium consisted of Murashige and Skoog's inorganic salt formulation containing 0.1 ppm thiamine hydrochloride, 0.5 ppm pyridoxine hydrochloride, 0.5 ppm nicotic acid, 2 ppm glycine and 100 ppm inositol, adjusted at pH 6.0, to which was added 1.0% weight by volume of agar. The medium was used after being sterilized in the usual manner.

The explant was incubated at 25° C. in light of 2,000 lux. After about 3 weeks of culture, there were formed green-colored undifferentiated symbionts (deposited at the Depository in the Technical Center belonging to Nippon Paint Co., Ltd. under Deposition No. NP L-29).

About 1 g (wet weight) of the undifferentiated symbionts obtained above was transplanted in 100 ml of a liquid culture medium excepting agar, and incubated at 25° C. in light of 2,000 lux on a shaker with a shaking velocity of 80 rpm. After a month of culture, the medium was filtered to give about 5 g (wet weight) of undifferentiated symbionts.

The symbionts were crushed in a mortar and extracted three times with acetone for 8 hours in a Soxhelet extractor. The obtained acetone extracts were combined, concentrated to about 50 ml and shaken with the same volume of water and 100 ml of ethyl acetate in a separating funnel. The shaking was repeated several times after separating the ethyl acetate layer each time. The combined ethyl acetate layers were evaporated to give a concentrate.

Figure 1:
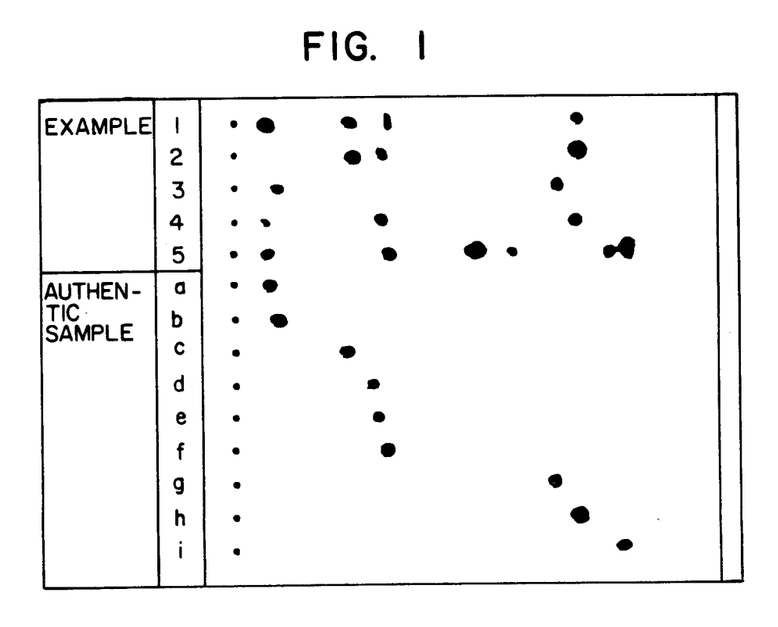

The thin-layer chromatogram of the concentrate under the following conditions is shown in FIG. 1 of the accompanying drawing: solvent, hexane/ether/formic acid = 130/80/20 (by volume); coloration, heating for 5 seconds after spraying 10% (by weight) sulfuric acid.

In FIG. 1, a to i are the chromatograms of the authentic samples in which a denotes salazinic acid, b stictic acid, c protocetraric acid, d fumarprotocetraric acid, e squamatic acid, f norstictic acid, q thiophanic acid, h usnic acid and i calycine, respectively.

Comparison of the chromatogram numbered 1 with those of authentic samples proves the presence of usnic acid, salazinic acid, protocetraric acid and norstictic acid.

EXAMPLE 2

A small piece with an area of about 0.5 $cm^3$ was cut from thallus of *Parmelia subramigera* (Parmelaceae, Lecanorales) collected at Hirakata-shi. The procedures in Example 1 was repeated using this small piece to give a concentrate, the chromatogram of which is shown in FIG. 1. (The culture is deposited under Deposition No. NP L-20.)

Comparison of the chromatogram numbered 2 with those of authentic samples proves the presence of usunic acid, protocetraric acid and fumarprotocetraric acid.

EXAMPLE 3

A small piece with an area of about 0.5 $cm^2$ was cut from thallus of *Pertusaria flavicans* (Pertusariaceae, Lecanorales) collected at Hirakata-shi. The procedures in Example 1 were repeated using this small piece to give a concentrate, the chromatogram of which is shown in FIG. 1. (The culture is deposited under Deposition No. NP L-19.)

Comparison of the chromatogram numbered 3 with those of authentic samples proves the presence of thiophanic acid and sticnic acid.

EXAMPLE 4

The procedures in Example 1 were repeated except that podetium of *Cladonia pseudomacilenta* (Cladoniaceae, Lecanorales) was used in place of thallus of *Usnea rubescens*. Chromatogram of the obtained concentrate is shown in FIG. 1. (The culture is deposited under Deposition No. NP L-16.)

Comparison of the chromatogram numbered 4 with those of authentic samples proves the presence of usnic acid and squamatic acid.

EXAMPLE 5

The procedures in Example 1 were repeated except that a small piece with an area of about 0.5 $cm^2$ cut from *Pseudocyphellaria aurata* (Stictaceae, Lecanorales) collected at Kyoto-shi was used in place of the thallus of *Usnea rubescens*. Chromatogram of the obtained concentrate is shown in FIG. 1. (The culture is deposited under Deposition No. NP L-2.)

Comparison of the chromatogram numbered 5 with those of authentic samples proves the presence of calycine, stictic acid and norstictic acid.

EXAMPLE 6 TO 29

Using the lichenous plants shown below, tissue culture was carried out in the same manner similar as in Example 1 to give undifferentiated symbionts, which were then cultured in liquid medium. Various compounds reported in the literature were proved in the culture.

| Example | Name | Location | Deposition No. |
|---|---|---|---|
| 6 | *Parmelia calvulifera* | Kyoto-shi | NP L-1 |
| 7 | *Parmelia squarrosa* | Kyoto-shi | NP L-3 |

-continued

| Example | Name | Location | Deposition No. |
|---|---|---|---|
| 8 | *Parmelia caperata* | Kyoto-shi | NP L-4 |
| 9 | *Menegazzia terebrata* | Kyoto-shi | NP L-5 |
| 10 | *Parmelia tinctorum* | Kyoto-shi | NP L-6 |
| 11 | *Parmelia entotheiochroa* | Kyoto-shi | NP L-7 |
| 12 | *Usnea dorogawaensis* | Kyoto-shi | NP L-8 |
| 13 | *Ramalina subgeniculata* | Kyoto-shi | NP L-9 |
| 14 | *Ramalina yasudae* | Kyoto-shi | NP L-11 |
| 15 | *Usnea rubicunda* | Kyoto-shi | NP L-12 |
| 16 | *Lobaria orientalis* | Toyama-ken | NP L-13 |
| 17 | *Alectoria ochroleuoa* | Nagano-ken | NP L-14 |
| 18 | *Usnea aciculifera* | Kyoto-shi | NP L-15 |
| 19 | *Anaptychia microphylla* | Kyoto-shi | NP L-17 |
| 20 | *Pyxine endochyrysina* | Hirakata-shi | NP L-18 |
| 21 | *Lobaria discolor* | Shiga-ken | NP L-22 |
| 22 | *Parmelia rudecta* | Kyoto-shi | NP L-23 |
| 23 | *Cladonia rangiferina* | Kyoto-shi | NP L-24 |
| 24 | *Peltigera canina* | Kyoto-shi | NP L-25 |
| 25 | *Evernia esorediosa* | Furano-shi | NP L-45 |
| 26 | *Usnea diffracta* | Furano-shi | NP L-42 |
| 27 | *Cetraria juniperina* | Furano shi | NP L 53 |
| 28 | *Evernia prunastri* | Furano-shi | NP L-47 |
| 29 | *Usnea longissima* | Furano shi | NP L 39 |

EXAMPLE 30

About 1 g (wet weight) of the undifferentiated symbionts obtained in Example 1 was transplanted in culture medium with the same composition as in Example 1 and incubated at 25° C. in light of 2,000 lux passing continuously sterile air containing 1% of gaseous carbon dioxide at a rate of 5 ml/min. After 2 months of culture was obtained about 7 g (wet weight) of undifferentiated symbionts.

EXAMPLE 31

A small piece with an area of about 0.5 cm² was cut from thallus of *Parmelia caperata* (Parmeliaceae, Lecanorales) collected at Kyoto-shi and used for explant. The explant was placed aseptically on the same synthetic culture medium as in Example 1 and incubated at 25° C. in light of 1,000 lux. After about 3 weeks of culture, there were formed green-colored undifferentiated symbionts.

About 1 g (wet weight) of the symbionts obtained above were transplanted in culture medium with the same composition as in Example 1 and incubated at 25° C. in light of 1,000 lux passing continuously sterile air containing 1.5% of gaseous carbon dioxide at a rate of 5 ml/min. After 2 months of culture was obtained about 6 g (wet weight) of undifferentiated symbionts.

EXAMPLE 32

A small piece with a length of about 1 cm was cut from thallus of *Ramalina subgeniculata* (Osneaceae, Lecanorales) collected at Kyoto-shi and used for explant. The explant was placed aseptically on the same synthetic culture medium as in Example 1 and incubated at 25° C. in light of 2,000 lux. After about 3 weeks of culture, there were formed green-colored undifferentiated symbionts.

About 1 g (wet weight) of the symbionts obtained above were transplanted in culture medium with the same composition as in Example 1 and incubated at 25° C. in light of 2,000 lux passing continuously sterile air containing 1% of gaseous carbon dioxide at a rate of 5 ml/min. After 2 months of culture was obtained about 7 g (wet weight) of undifferentiated symbionts.

EXAMPLE 33

A small piece with an area of about 0.5 cm² was cut from thallus of *Pyxine endochrysina* (Physciaceae, Lecanorales) collected at Hirakata-shi and was used for an explant. The explant was placed aseptically on the same synthetic culture medium as in Example 1 and incubated at 25° C. in light of 1,000 lux. After about 3 weeks of culture, there were formed green-colored undifferentiated symbionts.

About 1 g (wet weight) of the symbionts obtained above were transplanted in a culture medium with the same composition as in Example 1 and incubated at 25° C. in light of 1,000 lux passing continuously sterile air containing 1.5% of gaseous carbon dioxide at a rate of 5 ml/min. After 2 months of culture was obtained about 6 g (wet weight) of undifferentiated symbionts.

EXAMPLE 34

The undifferentiated symbionts (3 g) obtained in Example 1 were suspended in a sterilized 3% sodium alginate solution (10 ml), which was added dropwise to a sterilized $CaCl_2$ solution (0.05M) to form a gel. The gel was chopped into divisions of immobilized lichens.

EXAMPLE 35

A small piece with an area of about 0.5 cm² was cut from thallus of *Parmeria caperata* (Parmeriaceae, Lecanorales) collected at Kyoto-shi and cultured in the same manner as in Example 1.

The obtained undifferentiated symbionts (3 g) were mixed with a 0.9% collagen fibril solution (80 ml) and formed into a film by casting. The film, after drying, was dipped in a 1% glutaraldehyde solution to give a bridged structure of immobilized lichen film.

EXAMPLE 36

A small piece with an area of about 0.5 cm² was cut from thallus of *Pertusaria flavicans* (Perlusariaceae, Lecanorales) collected at Hirakata-shi and cultured in the same manner as in Example 1.

The obtained undifferentiated symbionts (4 g) were mixed with acrylamide (4.5 g), N,N'-methylenebisacrylamide (0.05 g) and physiological saline solution to form a suspension. A mixture of the suspension, 5% aqueous methylaminopropionitrile (0.5 g) and 2.5% aqueous potassium persulfate solution (1 g) was kept at 10° C. for 30 minutes to form a gel. The gel was crushed into particles of immobilized lichens.

EXAMPLE 37

A small piece with an area of about 0.5 cm² was cut from thallus of *Pixine endochrysine* (Physiaceae, Lecanorales) collected at Hirakata-shi was cultured in the same manner as in Example 1.

The obtained undifferentiated symbionts (5 g) of *Pixine endochrysina* were suspended in a phosphate buffer (10 ml) of pH 7.5. Buffered ion-exchange resins (Diaion HP-10, 10 ml) of pH 7.0 were added to the suspension. The mixture was shaken overnight at 30° C. with a velocity of 220 rpm, decanted, washed several times with phosphate buffer by decantation in order to remove unreacted symbionts and pressed to give immobilized lichen particles.

What is claimed is:

1. A process for preparing aromatic lichenous substances which consists essentially of culturing an undifferentiated symbiotic combination of alga and fungus cells obtained directly from a lichen explant in a culture media under appropriate conditions and for a sufficient period of time to allow production of at least one of the said lichenous substances and recovering at least one of said lichenous substances from said media.

2. A process according to claim 1, said lichen flora is *Cladonia pseudomacilenta*.

3. The process according to claim 2, wherein the lichenous substance recovered is usnic acid and squamatic acid.

4. The process according to claim 1, wherein the culturing is performed in light.

5. The process according to claim 1, wherein the culturing is performed under irradiation with light of 500 to 10,000 lux.

6. The process according to claim 1, wherein the culturing is performed in the air enriched with carbon dioxide.

7. The process according to claim 6, wherein the air enriched with carbon dioxide contains carbon dioxide in a concentration of 0.1 to 5% by volume.

8. The process according to claim 1, wherein the aromatic lichenous substances are recovered by solvent extraction.

9. The process according to claim 1, wherein the produced lichenous substance is selected from the group consisting of depsidones, depsides, diphenyleneoxides, vulpinic acids, anthraquinones, phenanthrenequinones, triterpenes, tetronic acids and xanthones.

* * * * *